United States Patent
Leveille et al.

(10) Patent No.: US 6,452,673 B1
(45) Date of Patent: Sep. 17, 2002

(54) MULTIPLE INPUT FLOW CELL WITH SINGLE FLUID PATH

(75) Inventors: Michael J. Leveille, Northbridge, MA (US); Joseph M. DeLuca, Mendon, MA (US); Charles T. Murphy, North Attleboro, MA (US); Robert J. Karol, Marlboro, MA (US)

(73) Assignee: Waters Investments Limited

( * ) Notice: Subject to any disclaimer, the term of this patent is extended or adjusted under 35 U.S.C. 154(b) by 0 days.

(21) Appl. No.: 09/707,786

(22) Filed: Nov. 7, 2000

(51) Int. Cl.⁷ .................................................. G01N 4/10
(52) U.S. Cl. ........................ 356/246; 356/244; 356/213; 73/865.5; 73/854.33
(58) Field of Search ................................. 356/244, 246, 356/39, 73, 410, 411, 213; 250/257, 576; 210/198.2; 422/52, 70; 73/865.5

(56) References Cited

U.S. PATENT DOCUMENTS

| | | | | |
|---|---|---|---|---|
| 3,954,341 A | * | 5/1976 | Uffenheimer | 250/576 |
| 4,634,574 A | * | 1/1987 | Spurlin et al. | 422/52 |
| 4,822,166 A | * | 4/1989 | Rossiter | 356/246 |
| 4,966,969 A | * | 10/1990 | Allington et al. | 210/198.2 |
| 5,073,345 A | * | 12/1991 | Scott et al. | 422/70 |
| 5,517,870 A | * | 5/1996 | Kurimura et al. | 73/865.5 |

* cited by examiner

Primary Examiner—Frank G. Font
Assistant Examiner—Sang H. Nguyen
(74) Attorney, Agent, or Firm—Brian Michaelis; John Serio

(57) ABSTRACT

A chromatographic flow cell having the capacity to handle fluid flow from one or more chromatographic systems, at widely varying flow rates without the need to change flow cells or detectors. The flow cell itself acts as a tee where two or more fluidic inlet lines intersect with a common inlet channel. The common inlet channel is configured so that the diameter and length minimizes the total volume, unswept volume, bandspreading, and backpressure. The common outlet channel, inlet lines and the outlet line are sized to provide for adequate fluidic handling at the varied flow rates.

10 Claims, 4 Drawing Sheets

MULTIPLE INPUT FLOW CELL WITH SINGLE FLUID PATH

FIELD OF INVENTION

The present invention relates to a method of chromatographic chemical analysis, more particularly to the design of multiple fluidic input flow cells for use in photometric measurements.

BACKGROUND OF THE INVENTION

It is well known to measure an analyte of interest by photometric detection on fluid flowing from one or more chromatographic systems. To effect such measurement at widely varying flow rates presents the need to change flow cells and/or detectors. The changing of flow cells or detectors is both costly and time consuming. Several approaches to solve the problems that occur with varying flow rates with flow cells in the prior art have been attempted with certain limitations.

For example the use of a tee where there are two or more fluidic input lines entering into the tee and a single fluidic line exiting from the tee and into the flow cell is illustrated in FIG. 1. This method can be utilized when the internal diameter of the fluidic line exiting from the tee to the flow cell inlet is sized to handle the flow rates required from the two or more fluidic lines entering the tee. This approach is acceptable if the flow rates of the fluidic lines entering the tee are comparable and the same solvents are being used. A major disadvantage of this method occurs when the flow rates diverge, such as in the case of analytical flow rates which are approximately 1.0 ml/min, and preparative flow rates which are approximately 150 ml/min. If the flow rates are vastly different, such as in the above preparative flow rates, a fluidic line configured for preparative analysis would not be adaptable for analytical use. Attempts to utilize a preparative cell for analytical work results in problems such as chromatographic bandspreading. Conversely, an exiting fluidic line sized for analytical flow rates can cause damage to the column due to the very high backpressures if a preparative use is untertaken. The foregoing problem may be addressed by selecting an internal diameter tubing that will yield acceptable results for both preparative and analytical uses. However, as a practical matter selecting a tubing that will function in both high and low flow rate applications can be difficult to undertake without sacrificing the performance of the flow cell. Additionally, this approach creates the need for multiple fluidic interfaces.

Another method within the prior art is to use two detectors each with its own single inlet flow cell. Each of the flow cells would have different tubing internal diameters sized to accommodate either low or high flow rates. The flow cell for low flow rates could be used for method development and screening while the cell configured for higher flow rates would be used for high throughput analysis and or purification. The problem with this approach is that the detector flow cell combination used for the method development is not the same as that used for analysis or purification. The expense associated with purchasing and maintaining two detectors renders this approach impracticable.

Another approach is to use a single detector and interchange flow cells. In this approach the flow cell utilized is dependent upon the flow rate and type of analysis required. There are several limitations of this approach. The degree of automation within the chromatographic system is reduced because of the need to disturb the detector in order to place a different flow cell within the chromatographic system. Another limitation of this approach is that, while the same detector is used, the potential for variation in the method scale up is high due to utilizing two flow cells.

Consequently, there are numerous limitations associated with prior approaches to solve the problems caused by the variation of flow rates within a chromatography system. Most notably, the prior art suffers from several limitations such as cost, scalability, automation, and validation of the chromatography system.

SUMMARY OF THE INVENTION

The present invention provides a chromatographic flow cell having the capacity to handle fluid flow from one or more chromatographic streams, at widely varying flow rates, without the need to change flow cells or detectors.

According to the invention, the flow cell itself acts as a tee where two or more fluidic inlet lines intersect with a common inlet channel. The size of the common inlet channel is such that the diameter and length are configured to minimize the total volume, unswept volume, bandspreading, and backpressure over the varied range of flow rates. The common outlet channel and the outlet line are sized to provide for adequate fluidic handling at the varied flow rates.

The selections of the flow rates used with the flow cell according to the present invention are controlled by the use of directing valves. The user controls the valves either manually or through an automation scheme. The valves are used to direct the sample stream from the injector of the chromatographic system to either a high flow rate or a low flow rate path. Both flow rate paths are in fluidic communication with their respective high or low flow rate inlets of the flow cell. The flow cell contains a common channel that is in communication with both the high and low flow rate inlets. Features of the invention include provisions of a flow cell that does not require a change of detectors over a varied range of flow rates. Bandspreading, for analytical work, is avoided with the flow cell, according to the invention by configuring the common inlet channel with the proper diameter and length. Damage to the column as a result of back pressure is prevented by having a outlet channel that can handle both high and low flow rates. The frequency of validation of the chromatography system is decreased by the utilization of the same flow cell and detector. The cost to the user is greatly reduced by having a single detector that handles both high and low flow rate systems.

BRIEF DESCRIPTION OF THE DRAWINGS

The foregoing and other features and advantages of the present invention will be more fully-understood from the following detailed description of illustrative embodiments, taken in conjunction with the accompanying drawings in which:

FIG. 2b shows an enlarged detail of A of FIG. 2a.

FIG. 3b shows an enlarged detail of A of FIG. 3a.

DETAILED DESCRIPTION OF THE INVENTION

Figure 1:
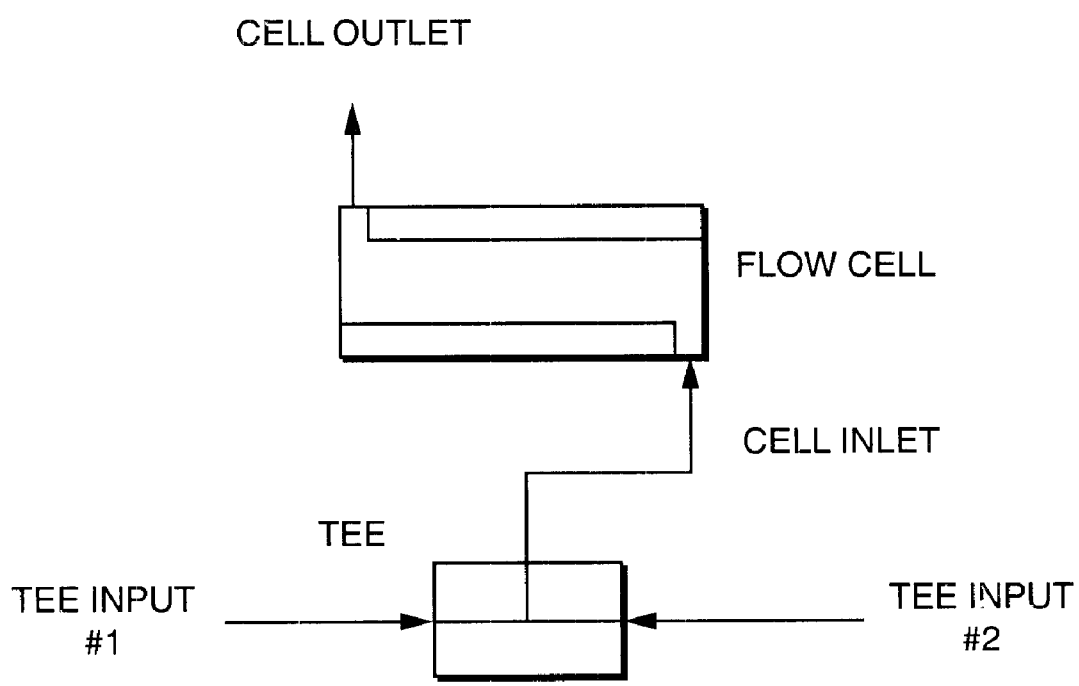
FIG. 1 shows a schematic drawing of the prior art.
Figure 2A:
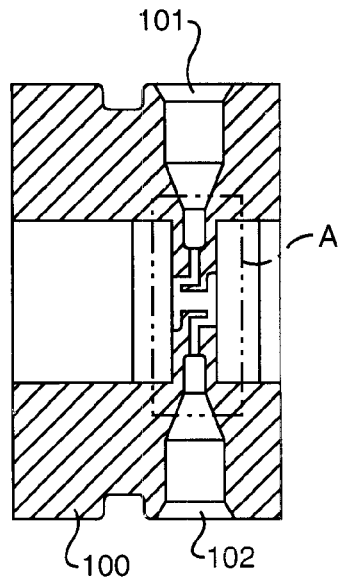
FIG. 2a shows a side sectioned schematic drawing of the present invention.
Figure 2C:
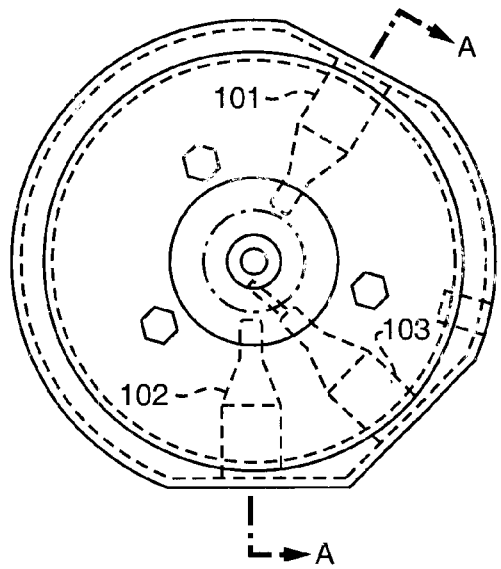
FIG. 2c shows a top plan view with features in phantom of the present invention

Referring in detail to the drawings, a flow cell utilizing multiple fluidic ports of the present invention is shown in section in FIG. 2a. It comprises a cell body 100 that is formed from stainless steel, however, it can also be formed from materials such as titanium, PEEK, or other materials known in the art that are inert to the sample substance and solvents utilized. The cell body 100 contains within it an outlet port 101, a first inlet port 102 and a second inlet port 103. The outlet port 101 is configured to receive an outlet line (not shown). The outlet port 101 and the outlet line are configured to provide for adequate fluidic handling up to flow rates of approximately 150 ml/min The first inlet port 102 can be configured to provide for adequate fluidic handling of either high flow rates 150 ml/min to adequate fluidic handling of low flow rates <0.5 ml/min. The second inlet port 103 can be of configured to provide for adequate fluidic handling of either high flow rates 150 ml/min to adequate fluidic handling of low flow rates <0.5 ml/min. The first inlet port 102 and the second inlet port 103 are configured to receive a first inlet line and a second inlet line (not shown) for adequate fluidic handling of either of the appropriate (i.e. high or low) flow rates The cell body 100 has a common inlet channel 104. The common inlet channel 104 is configured with a diameter and length have been selected to minimize the total volume, unswept volume, bandspreading, and backpressure over the range of flow rates generally employed within the intended application (<0.5 ml/min to 150 ml/min).

Backpressure damage to the chromatography system is prevented in the present invention by configuring the outlet port 101 and the outlet line to handle both high and low flow rates. The intersection of the inlet lines within the common inlet channel 104 reduces the amount of unswept volumes by the placement of the low flow rate inlet close to the end of the common inlet channel 104 as shown in FIG. 3b. The elimination of additional components such as a Tee and the union of the high and low flow rate lines directly into the flow cell 100 minimize the total volume thus reducing bandspreading.

Figure 2B:
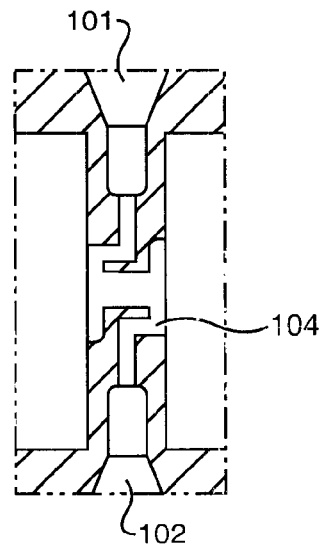

Referring now to FIGS. 2a and 2b, in an illustrative embodiment of the present invention, the dimension of the common inlet channel 104 is approximately 0.022 inches in internal diameter and approximately 0.055 inches in length. The fluidic outlet line is approximately 0.040 inches in internal diameter. The internal diameter of the first fluidic inlet line in this illustrative embodiment is approximately 0.009 inches and in this illustrative embodiment is the inlet line of the low flow rate. The internal diameter of the second fluidic inlet line is approximately 0.040 inches and in this illustrative embodiment is the inlet line of the high flow rate. In the illustrative embodiment utilizing the above dimension, the backpressure experienced at the column, when using an 80/20 mixture of IPA/$H_2O$ at a flow rate of 150 ml/min, was measured at approximately 260 psi.

Figure 3A:
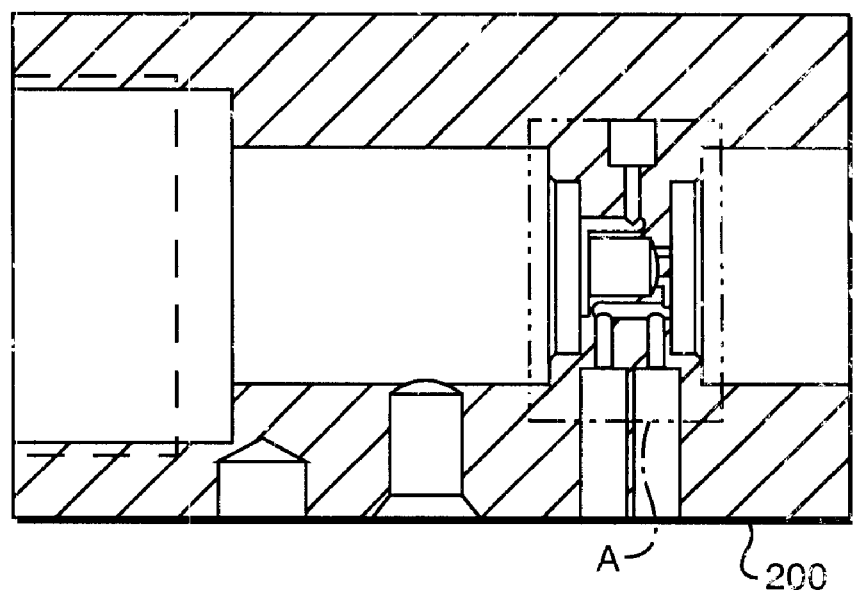
FIG. 3a shows an alternative embodiment of the present invention.
Figure 3B:
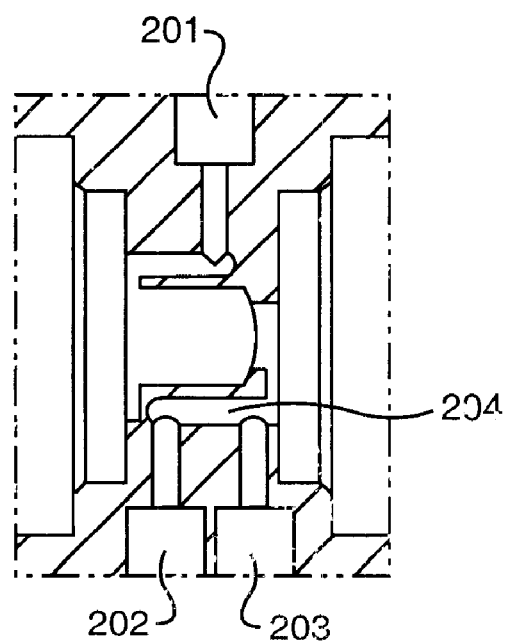

Turning now to FIGS. 3a and 3b an alternative embodiment of a flow cell utilizing multiple fluidic ports of the present invention is shown in section in FIG. 2a. It comprises a cell body 200 that is formed from stainless steel, however, it can also be formed from materials such as titanium, PEEK, or other materials known in the art that are inert to the sample substance and solvents utilized. The cell body 200 contains within it an outlet port 201, a first inlet port 202 and a second inlet port 203. The outlet port 201 is configured to receive an outlet line (not shown). The outlet port 201 and the outlet line are configured to provide for adequate fluidic handling at the flow rate 150 ml/min. The first inlet port 202 being positioned adjacent to the second inlet port 203 can be configured to provide for adequate fluidic handling of either high flow rates 150 ml/min to adequate fluidic handling of low flow rates <0.5 ml/min. The second inlet port 203 being within the same horizontal plane and adjacent to the first inlet port 202 can be of configured to provide for adequate fluidic handling of either high flow rates 150 ml/min to adequate fluidic handling of low flow rates <0.5 ml/min. The first inlet port 202 and the second inlet port 203 can be configured to receive a first inlet line and a second inlet line (not shown) for adequate fluidic handling of either high flow rates 150 ml/min to adequate fluidic handling of low flow rates <0.5 ml/min. The cell body 200 has a common inlet channel 204. The common inlet channel 204 is configured such that the diameter and length have been selected to minimize the total volume, unswept volume, bandspreading, and backpressure over the range of flow rates generally employed within the intended application (<0.5 ml/min to 150 ml/min).

Figure 4:
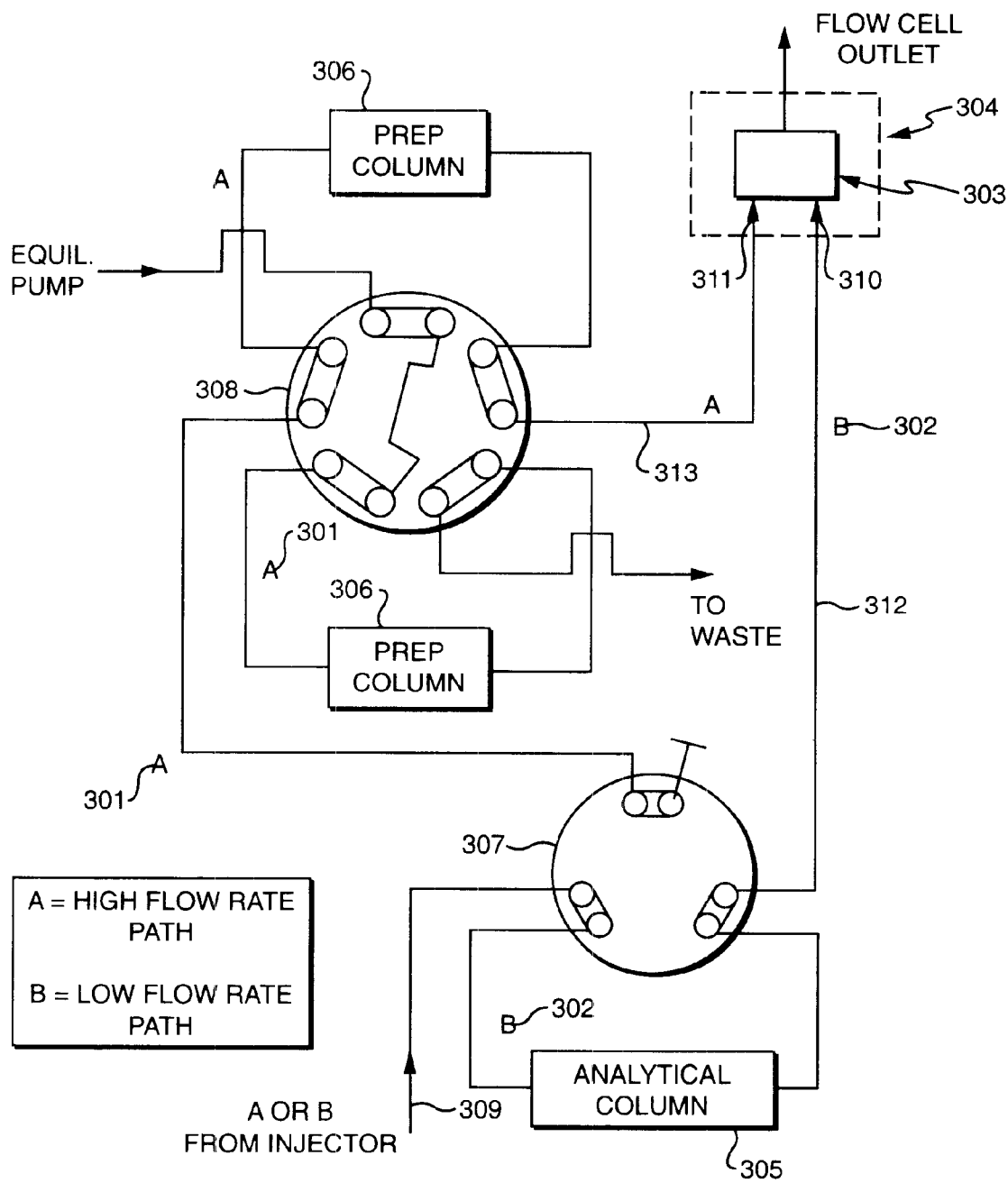
FIG. 4 shows a schematic of the present invention within a particular system application.

Referring to FIG. 4 a schematic of the chromatography system is shown with the illustrative flow cell positioned within a configuration allowing for a high flow rate path 301 and a low flow rate path 302 A flow cell 303 according to the present invention is configured within a chromatography system to allow the use of a detector 304 for analysis of either a sample from a analytical column 305 or a preparative column 306. The chromatography system has a first valve 307 and a second valve 308. The first valve 307 is in fluidic communication with an injector 309. The injector 309 delivers a high rate flow or a low rate flow. The valve 307 directs the flow to either the high flow path rate 301 or the low rate flow path 302 depending on the application and dead-ends the flow path not in use. In the illustrative embodiment depicted in FIG. 4, the valve 307 is positioned to direct the fluid to a low flow rate path 302 through the analytical column 305 of the chromatography system. The fluid exits the analytical column 305 and is directed by the valve 307 to a first inlet line 312. The first inlet line 312 is in fluidic communication with a low flow rate inlet 310. The first inlet line 312 and the low flow rate inlet 310 are configured for the adequate fluidic handling of low flow rates. The high flow rate path 301 in communication with valve 307 and valve 308 is dead-ended. In the alternative high flow rate path 301, the fluid from the injector 309 is directed by the valve 307 to the high flow rate path 301. The valve 307 is in fluidic communication with the second valve 308. The second valve 308 directs the fluid to one of the preparative column 306. The fluid exits the preparative column 306 and directed by the valve 308 to a second inlet line 313. The second inlet line 313 is in fluidic communication with a high flow rate inlet 311. The second inlet line 313 and the high flow rate inlet 311 are configured for the adequate fluidic handling of high flow rates.

Although the multiple port flow cell described in the illustrative embodiment uses only two inlet ports of circular cross section and certain dimensions, it should be appreciated by those skilled in the art that for other applications additional inlet ports can be implemented. Similarity, It should further be appreciated by those skilled in the art that multiple outlet ports can be implemented.

The present invention is not to be limited in scope by the illustrative embodiments described which are intended as specific illustrations of individual aspects of the invention, and functionally equivalent methods and components are within the scope of the invention Indeed, various modifications of the invention, in addition to those shown and described herein will be come apparent to those skilled in the art from the foregoing description. Such modifications are intended to fall within the scope of the appended claims.

What is claimed is:

1. A photometric flow cell comprising:

a cell body;

an outlet port contained within said cell body, said outlet port including an outlet channel configured to provide varied flow rates of fluid;

a first inlet port and a second inlet port adjacent to said first inlet port;

said first inlet port and said second inlet port contained within said cell body, and intersecting with a common inlet channel;

said common inlet channel contained within said cell body allowing the passage of fluids from said first inlet port or said second inlet port wherein said common inlet channel is in fluid communication with said outlet channel to minimize total volume, unswept volume, bandspreading and backpressure over a varied range of flow rates.

2. The photometric flow cell according to claim 1, wherein said outlet port is configured to handle both high flow rates and low flow rates.

3. The photometric flow cell according to claim 1, wherein said first inlet port is configured to handle high flow rates.

4. The photometric flow cell according to claim 1, wherein said first inlet port is configured to handle low flow rates.

5. The photometric flow cell according to claim 1, wherein said second inlet port is configured to handle low flow rates.

6. The photometric measurement flow cell according to claim 1, wherein said second inlet port is configured to handle high flow rates.

7. The photometric flow cell according to claim 1, wherein said common inlet channel is configured to minimize total volume, unswept volume, bandspreading and backpressure of flow rates between 0.5 ml/min to 150 ml/min.

8. The photometric flow cell according to claim 1, wherein said flow cell has the capacity to handle fluid flow from one or more chromatographic systems, said chromatographic systems having flow rates between 0.5 ml/min to 150 ml/min.

9. A method of utilizing a singular flow cell to handle varied flow rates from a plurality of chromatographic systems, which comprises:

selecting a flow cell having multiple inlet ports, said inlet ports being adjacent and intersecting with a common inlet channel wherein said common inlet channel is configured to minimize total volume, unswept volume, bandspreading and backpressure over a varied range of flow rates;

configuring said inlet ports for high or low flow rates; and directing a fluid flow to an appropriate pathway by utilizing a directing valve.

10. A photometric flow cell comprising:

a cell body;

a plurality of outlet ports contained within said cell body;

a common outlet port contained within said cell body allowing for the passage of fluids, said common outlet port including a common outlet channel receiving fluids from said plurality of outlet ports;

a plurality of inlet ports contained within said cell body;

a common inlet channel contained within said cell body allowing for the passage of fluids, said common inlet channel receiving fluids from said plurality of inlet ports, wherein said common inlet channel is configured to minimize total volume, unswept volume, bandspreading and backpressure over the varied range of flow rates; and said common inlet channel exiting fluids through said outlet ports.

* * * * *